United States Patent
Ebisawa

(10) Patent No.: US 7,533,988 B2
(45) Date of Patent: May 19, 2009

(54) EYESHOT DETECTION DEVICE USING DISTANCE IMAGE SENSOR

(75) Inventor: Yoshinobu Ebisawa, Hamamatsu (JP)

(73) Assignee: National University Corporation Shizuoka University (JP)

( * ) Notice: Subject to any disclaimer, the term of this patent is extended or adjusted under 35 U.S.C. 154(b) by 267 days.

(21) Appl. No.: 11/464,690

(22) Filed: Aug. 15, 2006

(65) Prior Publication Data

US 2007/0014552 A1     Jan. 18, 2007

Related U.S. Application Data

(63) Continuation-in-part of application No. PCT/JP2005/002661, filed on Feb. 14, 2005.

(30) Foreign Application Priority Data

Feb. 17, 2004    (JP)   ............................ P2004-039495

(51) Int. Cl.
     *A61B 3/10*          (2006.01)
     *A61B 3/14*          (2006.01)

(52) U.S. Cl. ........................ 351/206; 351/205; 351/208

(58) Field of Classification Search ................. 351/206, 351/205, 208
See application file for complete search history.

(56) References Cited

U.S. PATENT DOCUMENTS

| | | | | |
|---|---|---|---|---|
| 4,834,528 A | * | 5/1989 | Howland et al. | ............ 351/211 |
| 2002/0109701 A1 | * | 8/2002 | Deering | ...................... 345/581 |

FOREIGN PATENT DOCUMENTS

| | | |
|---|---|---|
| DE | 199 53 835 | 5/2001 |
| JP | 5-199995 | 8/1993 |
| JP | 05199995 A | * 8/1993 |
| JP | 6-189906 | 7/1994 |
| JP | 7-61314 | 7/1995 |
| JP | 8-238222 | 9/1996 |
| JP | 2739331 | 1/1998 |

(Continued)

OTHER PUBLICATIONS

International Search Report dated May 17, 2005.

*Primary Examiner*—Jessica T Stultz
*Assistant Examiner*—Mahidere S Sahle
(74) *Attorney, Agent, or Firm*—Ostrolenk, Faber, Gerb & Soffen, LLP

(57) ABSTRACT

An object of the present invention is, when determining a line-of-sight vector of a subject, to identify a three-dimensional position of a pupil center or corneal reflection center thereof. The line-of-sight vector is determined by measuring a distance from a camera to the pupil center or corneal reflection center of the subject using a two-dimensional CMOS distance image sensor by a light time-of-flight method and obtaining position information of the pupil center and corneal reflection center of the subject using the distance image sensor. If a position and a direction of the camera are identified, a camera-pupil center vector is determined from image information of the pupil center of the subject. Since the camera-pupil center distance has been measured, a pupil center position in a three-dimensional space is determined from the above information. Combining this with two line-of-sight vectors determines a position where line-of-sight vectors intersect, or a view-point.

4 Claims, 6 Drawing Sheets

FOREIGN PATENT DOCUMENTS

| | | |
|---|---|---|
| JP | 10-66678 | 3/1998 |
| JP | 10-509933 | 9/1998 |
| JP | 11-76165 | 3/1999 |
| JP | 2003-186411 | 7/2003 |
| JP | 2003-325455 | 11/2003 |

* cited by examiner (a)  (b)

US 7,533,988 B2

EYESHOT DETECTION DEVICE USING DISTANCE IMAGE SENSOR

CROSS-REFERENCE TO RELATED APPLICATIONS

This is a continuation-in-part application of application Ser. No. PCT/JP2005/002661 filed on Feb. 14, 2005, now pending, and incorporated by reference in its entirety.

BACKGROUND OF THE INVENTION

1. Field of the Invention

The present invention relates to a method and a device that correctly detect a line-of-sight direction of a subject without contact.

2. Related Background Art

In order to correctly detect a line-of-sight direction of a subject without contact, information about coordinates of a pupil or an eyeball center in a three-dimensional space and an angle formed by a straight line connecting the coordinates thereof and a camera and a line-of-sight is required. Conventionally, a three-dimensional position of a pupil has been detected by the trigonometric method using two wide angle cameras (See, for example, Patent Document 1) or an eyeball center has been estimated by attaching at least three markers on a face (See, for example, Patent Document 2). However, aforementioned methods have problems such as needing at least two cameras, cumbersome camera calibration of stereo cameras.

An ultrasonic range finder is known as a method for finding a distance from a camera to a subject (See, for example, Patent Documents 3 and 4).

In this case, by mounting an ultrasonic transmitter close to a camera, emitting an ultrasonic wave, measuring a time required to return after reflecting on an eye, and multiplying the time by a velocity of the ultrasonic wave and dividing by 2, the distance from the camera to the eye can be determined. However, the distance to a pupil cannot be correctly measured by a TOF (Time of flight) method using such an ultrasonic wave, because the ultrasonic wave actually reflects in a wide range around an eye due to problems such as weak directivity of the ultrasonic wave.

[Patent Document 1] Japanese Patent No. 2739331

[Patent Document 2] Japanese Patent Application Laid-open No. Hei 10-066678

[Patent Document 3] Japanese Patent Application Laid-open No. 2003-186411

[Patent Document 4] Translated National Publication of Patent Application No. Hei 10-509933

SUMMARY OF THE INVENTION

An object of the present invention is to identify a three-dimensional position of a pupil from a direction of a camera, a distance from the camera to the pupil, and an zoom ratio determined by the distance. Another object of the present invention is to determine, based on a line-of-sight vector determined basically from a relative positional relationship of a pupil center and corneal reflection center in an image, a focused point (view point) of a subject from an intersection of the line-of-sight vector and a known visual object plane. In addition, a still another object of the present invention is to determine, from two pupil line-of-sight vectors, an intersecting position of the line-of-sight vectors, that is, a focused point (view point) of a subject.

To this end, according to the present invention, instead of an ultrasonic wave, light is emitted to measure (light time-of-flight measurement) a delay time till the light returns after reflecting on an object and the delay time is multiplied by a propagation velocity of light so that not only the distance to the object can be measured with respect to each pixel, but also a camera that can take an image ordinarily is used.

The camera has an image sensor in which CMOS sensors (image sensors) that can respond quickly are arranged two-dimensionally. To make distance measurement, a physical object is irradiated with a pulsed light and a time difference between an irradiated light and a reflected light thereof is measured to determine the distance. Various methods can be considered to measure the time difference. In one of the methods, a counter and a pulse signal source are provided, counting is started when irradiation is started, and the counting is stopped when a reflected light is at its peak.

DETAILED DESCRIPTION OF THE PREFERRED EMBODIMENTS

Figure 1:
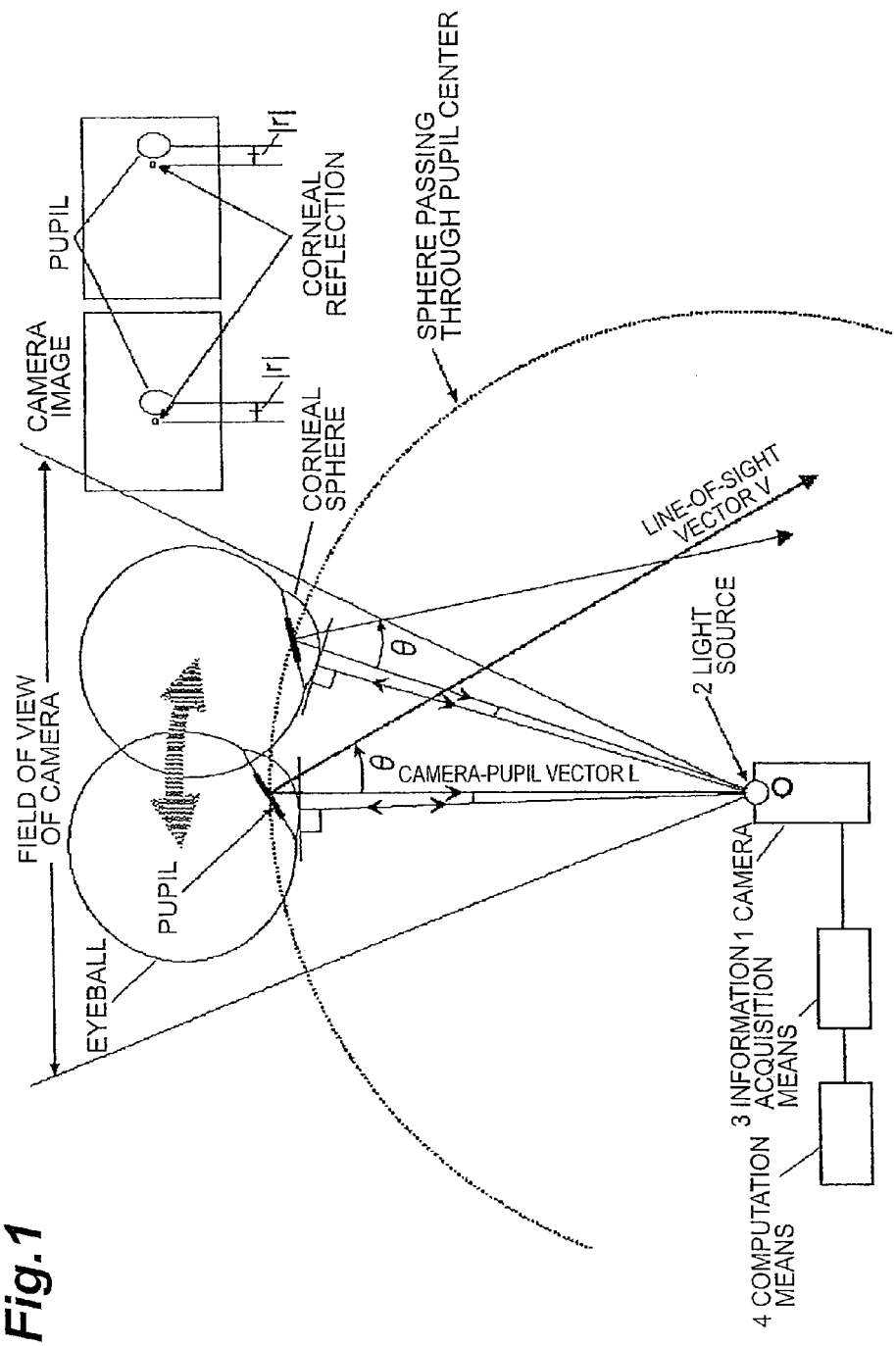
FIG. 1 is a diagram showing two-dimensionally relationships among a camera, a light source, and an eyeball.

As shown in FIG. 1, a line-of-sight detection device according to the present invention has a camera (1), a light source (2), an information acquisition means (3), and a computation means (4).

In the present embodiment, the line-of-sight detection device has the light source (2) close to the camera (1) or at a known position and causes the light source (2) to blink repeatedly at high speed. The camera (1) is generally a wide angle camera that can take just a picture of a whole face. The light source (2) is used as an invisible near infrared light source and, each time the light source (2) is turned on, distance measurement is made with respect to each pixel. More specifically, a light time-of-flight distance sensor described in Japanese Patent Application No. 2004-41057 can be used as the camera (1) and the distance sensor has a structure in which pixel circuits are arranged two-dimensionally so that distance image information can be generated by determining the delay time of a received light from a physical object and the distance to the object with respect to each pixel, at the same time two-dimensional brightness image information of the object can be generated.

Based on the distance image information from the camera (1), the information acquisition means (3) determines the distance from the camera (1) to the pupil center or corneal reflection center of a subject. Here, even if distance measurement is made, due to a nature of the pupil itself, it is the distance up to an eyeground (retina) and measurement of the distance to the pupil is difficult. Since, on the other hand, corneal reflection of the light source (2) is very bright and distance measurement can be made almost unaffected by disturbance light depending on ingenuity, using the corneal reflection is preferable for the present invention because acquisition of a correct distance is facilitated. Note that, it is assumed for the sake of simplicity that the camera (1) and the light source (2) are at the same position and the distance from the camera (1) to a corneal surface (for the sake of simplicity, called a corneal reflection position) causing corneal reflection should be measured. Since the corneal reflection position is different from the pupil center position by a depth of several mm, the distance to the corneal reflection position may be considered to be the distance to the pupil center or corrected by an appropriate value. The distance from the camera (1) to the pupil center can be determined by the aforementioned method and, by examining properties of the camera (1) in advance, in a camera coordinate system in which the optical axis of the camera (1) is defined as a z axis, the horizontal axis as an x axis, and a vertical axis as a y axis, a direction in which the pupil center is viewed from the camera (1) can be found using pupil center coordinates in an image (brightness image information) of the camera (1) and together with the distance information from the camera (1) to the pupil, a three-dimensional position of the pupil center can be estimated. In this manner, the computation means (4) determines the three-dimensional position of the pupil center of the subject.

Furthermore, the computation means (4) estimates an angle formed by a straight line connecting the camera (1) and the pupil center and a line-of-sight (passing through the pupil center) from relative coordinates of the corneal reflection center and pupil center in the image. Since this relationship depends on the subject, the line-of-sight must be calibrated in advance. A line-of-sight calibration is performed by making a subject view at least a point whose three-dimensional position is known in the camera coordinate system and the light source (2) (camera) sequentially. To detect a line-of-sight, a relative position of the corneal reflection center and pupil center is converted into an angle using a calibration formula obtained from the line-of-sight calibration and the angle and the three-dimensional position of the corneal reflection are used to determine a line-of-sight formula. Also, the computation means (4) determines an intersection of a line-of-sight and a target object represented by the formula as a view-point.

Embodiment

Figure 5:
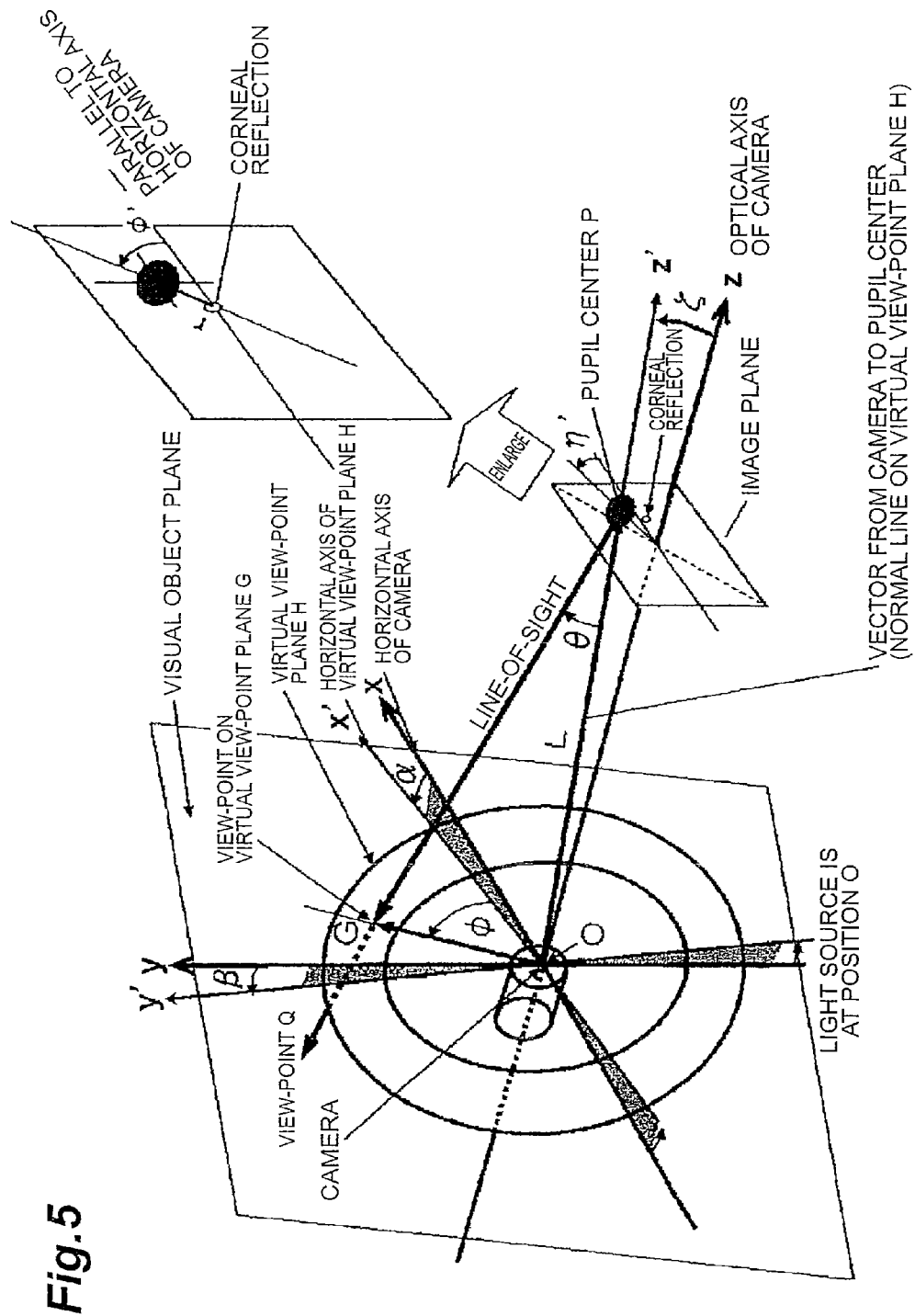
FIG. 5 is a diagram showing three-dimensionally relationships among the camera, the pupil center, and a line-of-sight vector.
Figure 6:
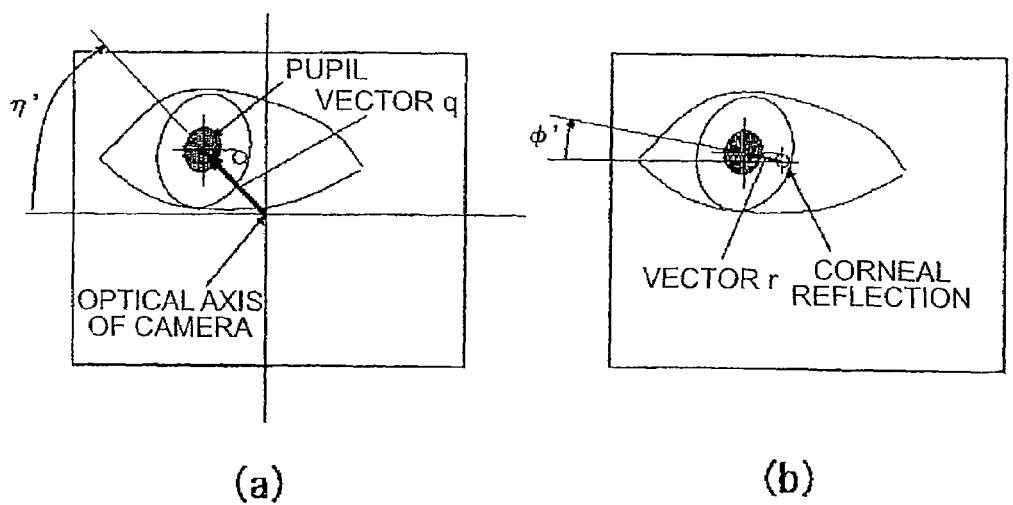
FIG. 6 is a diagram showing an angle η between a straight line connecting the pupil center and an optical axis of the camera and a horizontal axis, and an angle φ' between a straight line connecting the pupil center and a corneal reflection center and the horizontal axis.

It is assumed, as shown in FIG. 5, that the camera (1) and the light source (2) are arranged at origin O of the camera coordinate system, which is known in advance, and one or two eyes' image have been taken by the camera. Now, in an eye's image taken as shown in FIG. 6($a$), the computation means (4) detects a pupil and corneal reflection based on image processing and determines respective center coordinates. The computation means (4) calculates a size $|q|$ of a vector q connecting from coordinates corresponding to the camera optical axis in the image to the pupil center, an angle $\eta'$ formed by the vector and the horizontal axis, and three-dimensional coordinates of the pupil center from a distance L between the camera and pupil center measured by the camera (1). Here, the position angle $\xi$ of the pupil center viewed from the camera (1) is in a monotone increasing relationship to $|q|$ If this relationship can be represented by $\xi=g(|q|)$ using a function g and the function g is known, the computation means (4) can calculate $\xi$ by $\xi=g(|q|)$.

More specifically, assuming the distance between the camera and pupil center is L, in a coordinate system in which the optical axis of the camera (1) in FIG. 5 is defined as the z axis, the horizontal axis as the x axis, and the vertical axis as the y axis, the three-dimensional position P (xp, yp, zp) of the pupil center can be calculated as follows:

zp=L cos $\xi$ yp=L cos $\xi$ cos $\eta'$ xp=L cos $\xi$ sin $\eta'$

Figure 4:
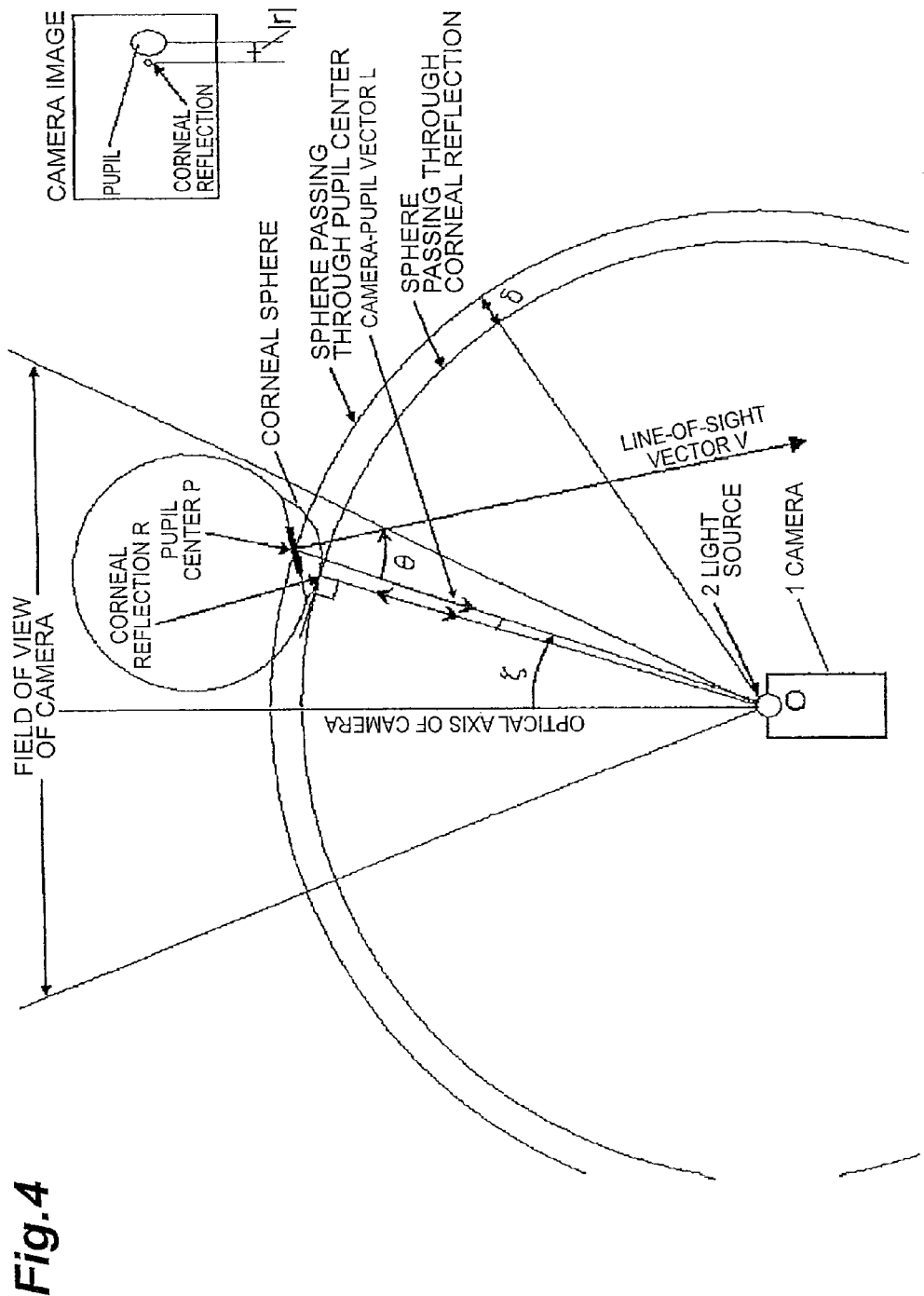
FIG. 4 is a diagram showing a position angle ξ of the pupil center viewed from the camera.

Here, as shown in FIG. 4, a property that, assuming a field-of-view angle of the camera (1) is known, the position angle $\xi$ of the pupil center viewed from the camera (1) is determined from coordinates of the pupil center in an image is used. Though there is a difference $\delta$ between the distance up to the pupil and the distance up to a position on cornea where corneal reflection occurs, the distance between the camera and pupil center is substituted by the distance between the camera and corneal reflection by considering this difference sufficiently small or corrected by an approximate estimated value $\delta$. The distance between the camera and corneal reflection is determined by detecting corneal reflection as an easily detectable bright small point near a pupil image and determining average distance information of pixels thereof.

Furthermore, the computation means (4) determines an angle $\theta$ formed by a straight line connecting the camera and pupil center and a line-of-sight from a distance $|r|$ between the corneal reflection center and pupil center in an image. The angle $\theta$ formed by a straight line connecting the camera and pupil center and a line-of-sight depends on the distance $|r|$ between the corneal reflection center and pupil center in an image and can be represented as $\theta=f(|r|)$.

Figure 2:
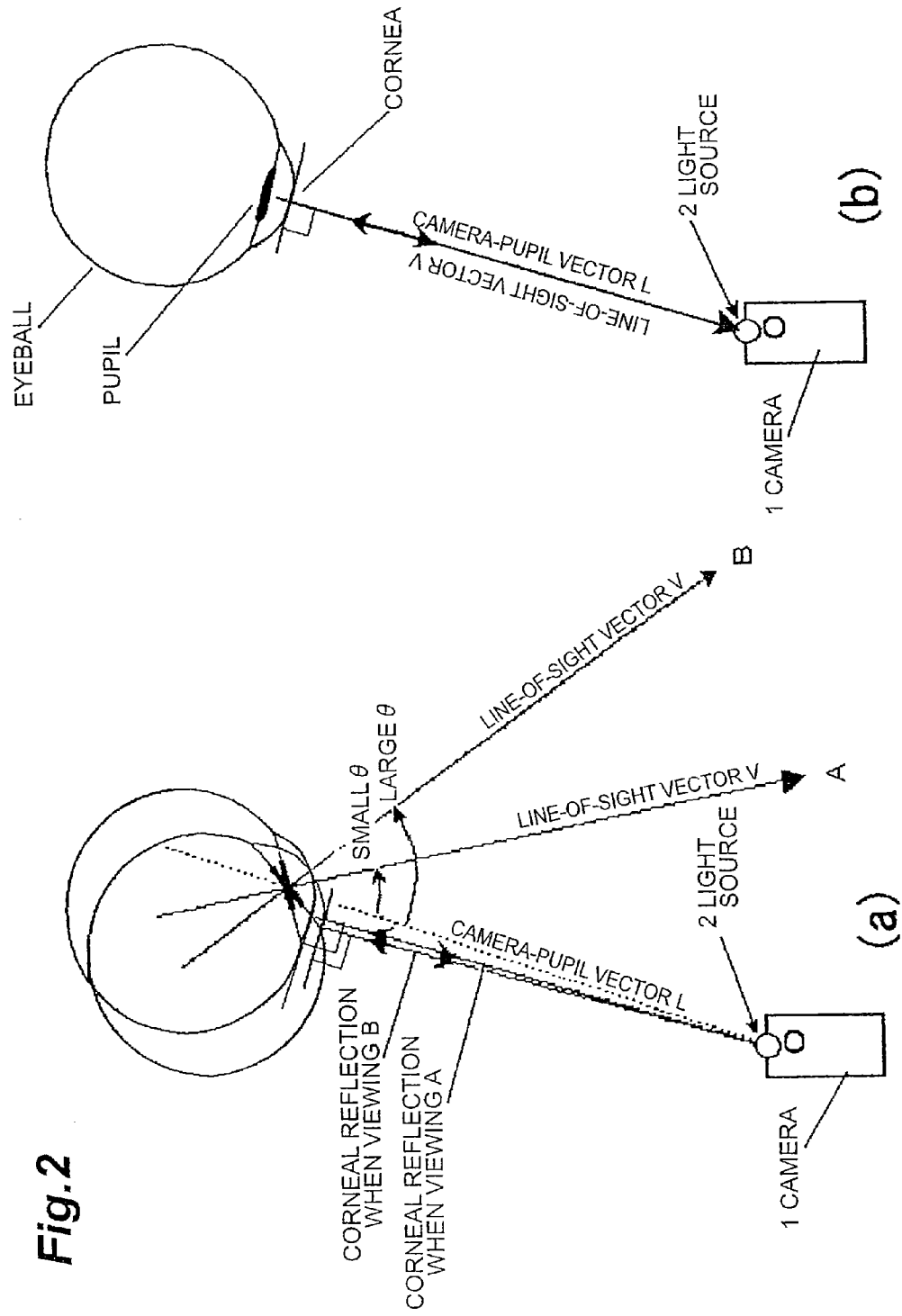
FIG. 2 is diagram showing the case in which a line-of-sight changes while a pupil center position is maintained.

That is, as shown in FIG. 2($a$), the distance $|r|$ between the corneal reflection center and pupil center in an image changes depending on varying sizes of $\theta$ and a relationship between $\theta$ and $|r|$ can generally be represented as a function like $|r|=f(\theta)$. Since the function is different with respect to each subject due to a different shape of eyeballs or the like, the function must be calibrated with respect to each subject. When the angle $\theta$ is small, generally $\theta$ and $|r|$ are directly proportional and a rough estimate can be made using an average value. In this case, a calibration is performed by making a subject gaze at a calibration point whose position is known in advance and finding a difference from the estimated position information. By providing several calibration points, a calibration can still be performed even when the angle $\theta$ is large. For example, assuming $\theta$ and r when a subject views O are $\theta_O$ and $|r_O|$ respectively, since $|r_O|=0$, a linear relationship $\theta=k |r|$ is assumed from $\theta$ and $|r|$ when a calibration point is viewed, and the coefficient k is determined. However, when the angle $\theta$ is so large that the corneal reflection center deviates from a corneal region into a scleral region of an eye, any calibration point is meaningless. (Detection of a line-of-sight in this case will be described later.)

Incidentally, when a line-of-sight vector is directed toward the camera (1), as shown in FIG. 2($b$), the pupil center and the corneal reflection center as viewed from the camera (1) agree and $|r|=0$. These pupil center and corneal reflection positions can be acquired by extracting them from a camera image. This processing is performed by the information acquisition means (3) and the information acquisition means (3) may be one incorporated in the camera (1). Also, computational processing such as functional operations is performed by the computation means (4) and the computation means (4) may be incorporated in the information acquisition means (3) or functionality thereof may be performed by a CPU inside a personal computer at a remote location.

Figure 3:
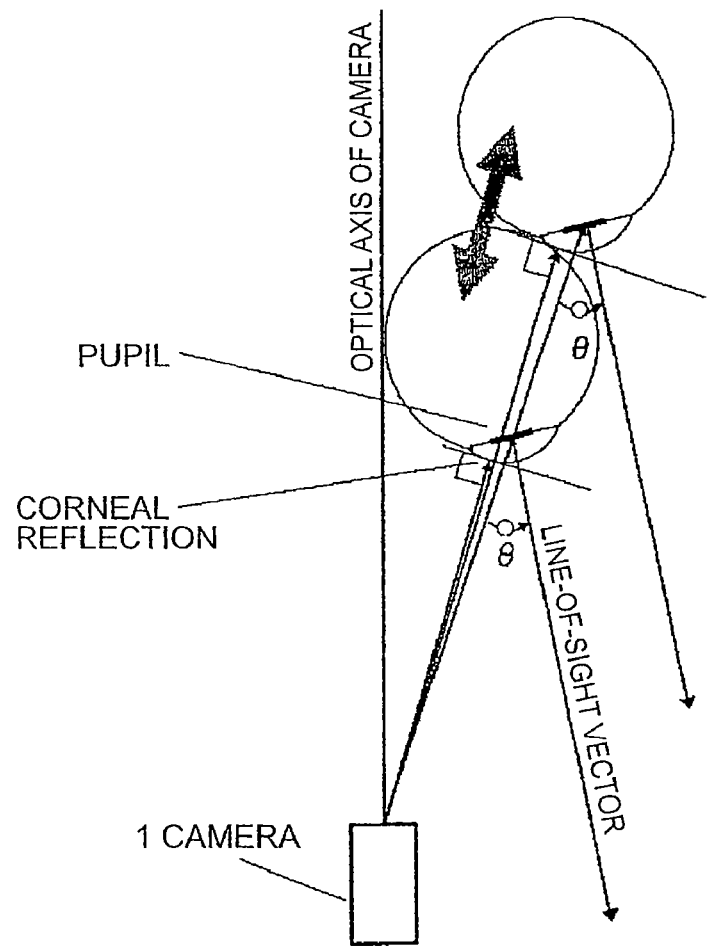
FIG. 3 is a diagram showing the case in which a distance from the camera to the pupil center changes while θ is maintained constant.

Now, as shown in FIG. 3, the distance from the camera (1) to the pupil center changes while θ is maintained constant, a relative distance between the corneal reflection center and pupil center changes. Since an apparent distance between the corneal reflection center and pupil center decreases when the distance from the camera (1) to the pupil center increases, this change is generally inversely proportional. Accordingly, this inverse proportional relationship or a relationship between the distance L and zoom ratio measured in advance should be used to correct |r|.

Next, the computation means (4) will detect an unknown view-point Q in the following manner.

In FIG. 5, a plane obtained by rotating (rotated by β turns around the x axis, and then rotated by α turns around the y' axis) a plane including a point O in which the z axis of the camera (1) is defined as a normal line around the point O while keeping the camera (1) horizontally so that a straight line OP becomes a normal line is assumed as a virtual view-point plane H. Now, when a subject views a point Q on a visual object plane, a line-of-sight PQ has an intersection at a point G in the plane H. Assuming an angle formed by a horizontal axis x' of the plane H and a vector OG is φ, φ can be considered to be equal to an angle φ' formed by a vector r directed from the corneal reflection center to the pupil center shown in FIG. 6(b) and the horizontal axis of the camera (1) (φ=φ').

Therefore, if, conversely, the pupil center P, θ, and φ are known, a line-of-sight formula and point G can be determined and, if a visual object plane formula is further known, the view-point Q can be determined as an intersection of the visual object plane and line-of-sight.

More specifically, $|OG|=|OP| \tan θ$ and a point G (XG', YG', 0) in an orthogonal coordinate system X', Y', and Z' of the virtual view-point plane H is determined by formulas shown below;

$XG'=|OG| \cos φ$ $YG'=|OG| \sin φ$

Then, in the orthogonal coordinate system of the plane H, coordinates of a point P are given by (|OP|, 0, 0) and a line-of-sight vector in the coordinate system is determined as a vector PG connecting from P to G as follows:

$PG=(XG', YG', -|OP|)$

This is also a directional vector of the line-of-sight vector in the orthogonal coordinate system of the plane H.

Furthermore, a directional vector (1x, 1y, 1z) of a vector OP in a camera coordinate system XYZ agrees with a Z' coordinate in the orthogonal coordinate system of the plane H. Now, if the Y' axis of the orthogonal coordinate system of the plane H is rotated by –β around the X' axis of the orthogonal coordinate system of the plane H so that the Y' axis agrees with the Y axis of the camera coordinate system, and then the X' axis of the orthogonal coordinate system of the plane H is rotated by –α around a new Y' axis of the orthogonal coordinate system of the plane H so that the X' axis agrees with the X axis of the camera coordinate system, the orthogonal coordinate system of the plane H will agree with the camera coordinate system. By performing the above described rotations of the coordinate system, a directional vector of the vector PG in the orthogonal coordinate system of the plane H is converted into a directional vector (sx, sy, sz) of a line-of-sight vector in the camera coordinate system, where $\cos α = 1z/(1x^2+1z^2)^{1/2}$ $\sin α = 1x/(1x^2+1z^2)^{1/2}$ $\cos β = (1x^2+1z^2)^{1/2}/(1x^2+1y^2+1^2)^{1/2}$ $\sin β = 1y/(1x^2+1y^2+1z^2)^{1/2}$ Then, using the obtained directional vector (sx, sy, sz), a line-of-sight formula in the camera coordinate system is represented by the formula shown below:

$(x-xp)/sx = (y-yp)/sy = (z-zp)/sz$

When the visual object is a plane and the formula thereof is given by the formula shown below, $m_x \cdot x + m_y \cdot y + m_z \cdot z + d = 0$ the view-point Q is determined by the above two formulas.

If, here, the visual object plane is unknown, line-of-sight vectors of both pupils are determined and then an intersection of both line-of-sight vectors is determined as the view-point Q. This intersection does not necessarily exist because of a twisted relationship of both line-of-sight vectors without intersection or a measurement error, and in such cases, an intersection should be determined as an approximate solution.

Here, a reason why a line-of-sight direction can be determined from relative coordinates of a corneal reflection and a pupil center will be described. In FIG. 1, a relationship among the camera (1), the light source (2), and an eyeball is illustrated two-dimensionally. Assuming that the position of the camera (1) and that of the light source (2) agree and a point thereof is denoted as O, if the eyeball is rotated around the point O while an angle θ formed by a straight line connecting the camera (1) and the pupil center and the line-of-sight is maintained, the distance from the point O to the pupil center P is kept as a constant value from the point O. In this case, the pupil and corneal reflection in the image move, but relative positions thereof do not change. The line-of-sight passes through the pupil center. The angle θ formed by a straight line passing through the camera O and the pupil center P and the line-of-sight is determined, as described above, from the distance |r| between the corneal reflection center and pupil center and the function f so that the line-of-sight is determined.

So far, the description has been provided under the assumption that a line-of-sight vector is determined from a pupil center and a corneal reflection center, but a line-of-sight vector can also be determined from ellipticity of a pupil, though accuracy of a line-of-sight vector becomes a little lower. In this case, a pupil is approximated as disc-shaped and a line-of-sight vector can be determined from a ratio of major axis and minor axis when viewed in a slanting direction and the direction of major axis or minor axis. Or, a method of determining a line-of-sight vector may be switched depending on θ; if θ is small, a line-of-sight vector is determined from the pupil center and corneal reflection center; if θ is large, a line-of-sight vector is determined from ellipticity of a pupil. For example, a line-of-sight detection device is constructed such that when a subject views in a direction about ±30 to 40 degrees from an axis connecting the camera (1) and pupil and a corneal reflection exists in an image, a line-of-sight is accurately determined from a relationship between the corneal reflection and pupil center, and when a viewing direction exceeds ±30 to 40 degrees and no corneal reflection exists, an approximate line-of-sight direction is determined from ellipticity of a pupil. This is an effective means if it is necessary to know correctly which part of an object presented in front of a face of a subject is viewed and it is not necessary to know correctly a line-of-sight direction when viewing sideways, and it becomes possible to detect a line-of-sight of about ±70 to 80 degrees.

That is, if a corneal reflection enters the scleral region of an eye, an image is generally taken that is larger than the corneal reflection and has a complicated shape. However, the image has a very high level of brightness like the corneal reflection. Hence, an approximate direction of a line-of-sight can also be estimated from ellipticity (long axis/short axis) of a pupil and a short axis direction. However, for example, whether viewing 40 degrees to the right or 40 degrees to the left, a pupil becomes equally a vertically long ellipse with the same ellipticity and thus it is impossible to distinguish whether viewing to the right or left. In such a case, to which side the white of an eye shines with respect to a pupil could become a means for distinguishing it. Moreover, by measuring the distance up to a portion where the white of an eye shone, a rough line-of-sight can still be detected when θ is large.

If the angle of a line-of-sight vector changes considerably, a line-of-sight can be detected with high accuracy by arranging a plurality of cameras (1) around a subject and determining a line-of-sight vector by selecting an image with small θ from the plurality of cameras (1).

As described above, if θ is large, a reflection image (generally a corneal reflection) of the light source (2) deviates from a corneal reflection region into a scleral region of the eye to become an irregular image (white eye reflection image), as distinct from the corneal reflection. However, also in this case, the image has a very high level of brightness and distance information regarding the image can be used in place of distance information up to the corneal reflection.

In addition, it is generally difficult to detect a pupil without illumination. However, the light source (2) used for distance measurement can be used to make pupil detection easier. Ideally, the light source should be arranged so as to surround an aperture of the camera (1) like a ring. If the light source (2) is arranged near the aperture of the camera (1) in this manner, the pupil's image tends to be taken brighter than surroundings thereof. However, if a whole face's image is taken, there are many portions that are taken brighter than the pupil and thus it is not necessarily simple to detect the pupil. In such a case, another light source is provided at a remote location from the camera aperture. With this light source, the pupil's image develops a tendency to be taken darker than surroundings thereof In this case, however, there are still portions that are taken darker than the pupil. Hence, by causing the light source near the aperture of the camera (1) and the remote light source to be turned on alternately by synchronizing with a video frame or field and finding a difference between an obtained face image of the brighter pupil and that of the darker pupil, the pupil can be made conspicuous, making detection of the pupil and that of the pupil center easier.

In this case, several methods of determining the distance to a pupil can be considered. If, as assumed, the position of the light source and that of the camera (1) are identical, it is appropriate to use distance information up to a corneal reflection when the light source near the aperture of the camera (1) is turned on (With such an arrangement, the ring-shaped light source thereof is mirrored small on cornea as a corneal reflection. Thus, regions of the corneal reflection are distinguished by binarization or the like and an average distance or the like is determined from pixels in the region, and the distance thus determined shall be the distance to the cornea.) However, it is also possible to measure a distance using a remote light source from the camera aperture. As one of such methods, a plurality of light sources are arranged at point symmetrical positions with respect to the center of aperture of the camera (1). For example, light sources are arranged at right and left positions or up and down positions. Since an intermediate position of these light sources agrees with the aperture center, the distance up to the corneal reflection is taken here also as an average distance to each light source and the distance thus determined or a corrected distance described above is used as the distance up to the pupil. Remote light sources from the aperture can also be arranged like a ring concentrically with light sources arranged as described above surrounding the aperture like a ring. Also in this case, because the center of the latter large ring agrees with the aperture center, the same thing as the above can be said.

Both of distance information determined from the light sources near the aperture of the camera (1) and remote light sources respectively can also be used.

INDUSTRIAL APPLICABILITY

1. Since line-of-sights of both eyes can be simultaneously measured using at least one camera and one light source, it becomes possible to measure an angle of convergence (an angle formed by line-of-sights of both eyes) and a view-point (an intersection of line-of-sights of both eyes) in a depth direction, and to know an approximate distance of what is currently being viewed. As a result, a view-point in a three-dimensional space can be found (a point where line-of-sights of both eyes intersect, 3D view-point).

2. A three-dimensional position of a pupil can be measured. The pupil is an origin of a line-of-sight and thus it becomes possible to know from where a user is viewing (instead of where a user is viewing). Therefore, the present invention is effective in a system in which it is necessary to exactly know a location from which a person is viewing.

(Conventionally, this has had to be realized by mounting a magnetic sensor or the like on a head and measuring movement of the head, but this method cannot measure the location of a pupil exactly, though mounting of a sensor on a head is required.)

3. Since there is no drive and a camera is fixed in the present method, realization thereof is easy.

In addition, when the camera is only sensitive enough, an aperture of the camera can be made smaller. A light source can also be miniaturized easily by producing a high-intensity one.

4. Since the camera can be miniaturized, it becomes possible to arrange a plurality of cameras around a subject and deal with an angle change of the head of the subject.

What is claimed is:

1. A line-of-sight detection device using a distance image sensor, comprising:

a camera equipped with a light time-of-flight distance image sensor in which image sensors are two-dimensionally arranged;

a light source generating a pulsed light;

wherein said light time-of-flight distance image sensor generates distance information with respect to each pixel of said image sensors by measuring a delay time of said pulsed light generated by said light source;

information acquisition means for obtaining, from output of the distance image sensor, image information of a pupil center and a corneal reflection center of a subject, and distance information from the distance image sensor to the pupil center or the corneal reflection center; and computation means for determining a three-dimensional position of the pupil center of the subject from the image information and distance information.

2. The line-of-sight detection device using the distance image sensor according to claim 1, wherein said computation means further determines a line-of-sight vector of the subject from the image information and distance information.

3. The line-of-sight detection device using the distance image sensor according to claim 2, wherein the computation means determines a line-of-sight vector by referring to elliptic information of a pupil and a direction in which a white eye reflection occurs with respect to the pupil when an intersection angle between a vector directed from the camera to the subject and the line-of-sight vector is large.

4. The line-of-sight detection device using the distance image sensor according to claims 2, comprising a plurality of cameras arranged around the subject, wherein the line-of-sight vector can be detected in a wider range by arranging said plurality of cameras so as to surround the subject.

* * * * *